United States Patent [19]

Ikariyama et al.

[11] Patent Number: 5,269,903
[45] Date of Patent: Dec. 14, 1993

[54] MICROBIOELECTRODE AND METHOD OF FABRICATING THE SAME

[76] Inventors: Yoshito Ikariyama, 4-choume, Namiki, Tokorosawa-shi, Saitama, 359; Shigero Yamuchi, 22-7-205, Ichiban-cho, Chiyoda-ku, Tokyo, 102, both of Japan

[21] Appl. No.: 779,194

[22] Filed: Oct. 22, 1991

Related U.S. Application Data

[63] Continuation-in-part of Ser. No. 294,661, Jan. 11, 1989, filed as PCT/JP88/00255, Mar. 11, 1988, abandoned.

[30] Foreign Application Priority Data

Mar. 13, 1987 [JP] Japan .................................. 62-56472
Dec. 3, 1987 [JP] Japan ................................ 62-304523

[51] Int. Cl.$^5$ ............................................. G01N 27/26
[52] U.S. Cl. .................................. 204/403; 204/415; 435/817; 435/288
[58] Field of Search ................ 204/403, 415; 435/817, 435/288

[56] References Cited

U.S. PATENT DOCUMENTS 4,545,382 10/1985 Higgins et al. ........................ 204/415
4,970,145 11/1990 Bennetto et al. ...................... 204/403

Primary Examiner—John Niebling
Assistant Examiner—Bruce F. Bell
Attorney, Agent, or Firm—Douglas W. Robinson

[57] ABSTRACT

Fine particles 1 of an electrically conductive material such as platinum black are being deposited electrolytically on the end surface of an electrically conductive material (base) such as platinum, with immersion of the conductive material in a solution containing both of a conductive material to produce porous deposition 1, e.g. platinum black, and a biofunctional material (biologically active substance) 2 such as an enzyme, so as to produce a microbioelectrode 7 having fine particle layer 1 and biologically active substance 2 incorporated therein, with significantly high surface area. This microbioelectrode can be compact in size and moreover, since the apparent surface area of the fine particles 1 of the conductive material is significantly large and a considerable amount of the biologically active material 2 can be incorporated and immobilized in the conductive fine particles 1, the intended trace target substance can be measured quickly and with high sensitivity even when it is in a trace amount of sample.

13 Claims, 11 Drawing Sheets

MICROBIOELECTRODE AND METHOD OF FABRICATING THE SAME

CROSS-REFERENCE TO RELATED APPLICATION

This is a continuation-in-part of U.S. Pat. application Ser. No. 07/294,661 filed on Jan. 11, 1989, now abandoned and International Application PCT/JP88/00255 filed on Mar. 11, 1988 and which designated the U.S.

FIELD OF THE INVENTION

The present invention relates to a microbioelectrode having high performance, and a method of manufacturing the same. Particularly, it relates to a method for preparation of a microbioelectrode having a diameter in the order of micrometer, which can enable one to manufacture a miniatuarized analytical instrument with high performance to secure real time measurement.

DESCRIPTION OF THE PRIOR ART

Biosensing electrode made predominantly of an immobilized enzyme and transducing electrode is well-known in the prior art. Recent attempts for the construction of such electrode have been made by immobilizing an enzyme on various transducing electrodes.

Hitherto, enzymes have been immobilized on supporting matrices by covalent coupling, physical adsorption or ionic binding. Most of the conventional supports have been made of polymeric membranes. These conventional enzyme membranes have been attached to the surfaces of transducing electrodes, e.g., oxygen electrodes or hydrogen peroxide electrodes.

Further, details of such techniques can be found in the book entitled "Biosensors Fundamentals and Applications", edited by A. D. F. Turner, I. Karube and G. S. Wilson; published from Oxford University Press, in 1988.

The use of immobilized enzymes in membrane form as the receptor materials for biosensing devices has demonstrated convenient analytical instruments, whereby a physiologically active substance can be easily detected and measured with high sensitivity and high selectivity. However, the preparation of such membranes has heretofore been time-consuming. Furthermore, such techniques are not readily adopted to fabricate miniaturized biosensors having diameter in the micrometer order.

Therefore, there has arisen a need for a method of preparing an enzyme-embodied electrode, i.e., an enzyme and electrode can be combined, so as to produce a microbioelectrode with high performance, wherein physiologically active substances can be determined with high accuracy and sensitivity.

Many attempts have been made to conquer these problems, as described below.

Keyes's patent (U.S. Pat. No. 3,839,175) discloses a process for electrolytical depositing and immobilizing an enzyme by inducing electrolytic migration of the enzyme in an aqueous dispersion thereof, and intercepting the migrating enzyme on an inert inorganic, porous, sorptive, dimensionally stable, fluid permeable supporting matrix to form a biologically active composite, where the supporting matrix is ceramic and has been formed by compacting and sintering refractory oxide powders such as alumina.

Freeman et al (U.S. Pat. No. 4,659,665) discloses a membrane or film containing a biologically active protein such as an enzyme, which is prepared from a polymer substituted with acyl hyrdazide groups, preferably an acrylamide/-methacrylamide copolymer in a given respective molar ratio, with acryl hydrazide group substitution, and the membrane being formed on an electrode, and crosslinked with a crosslinking agent to produce an enzyme electrode.

Japanese Patent Publication No. 84-052598 discloses fixing of enzymes on a polymer matrix, which matrix is set between two electrodes or envelopes of the electrodes. When a voltage of preferably 10 to 500 V is applied between the electrodes, the enzyme will move in the solution on electrophoresis and is fixed in the polymer. The similar proposal is disclosed in Japanese Patent publication No. 84-11186. In the above mentioned two patent, the matrix is placed on the insulating material, and the electrode and the supporting material are of different material.

Japanese Patent Publication No. 87-304424/43 discloses use of protein coated magnetic particles as a carrier for securing an enzyme on the electrode. Therefore, the carrier is not conductive.

Japanese Patent Publication No. 85-259356 discloses that an aluminum base is subjected to anodic oxidation with a high current density of 5 to 60 A/cm$^2$ in an acidic solution to form an anodic oxide film on the surface, and then immersed in a buffer solution containing an enzyme so as to adsorb the enzyme on the carrier comprising a barrier layer (280 to 300 Angstrom), a porous layer (53 micrometers) and a needle-like constitution layer (31 micrometers) formed on the base.

Japanese patent publication No. 81-163447 discloses an indirect glucose electrode in which hydrogen peroxide produced by the oxidation of glucose in the presence of glucose oxidase is oxidised at the surface of a platinum electrode to produce an oxidation current proportion to the substance concentration of the sample. The electrode comprises an electrically conductive carbon base supporting a layer of immobilised enzyme, e.g. an immobilised glucose oxidase. The electrically conductive base itself is of moulded graphite containing up to 10 parts by weight of a fluorocarbon resin as a binder, and onto which is deposited, e.g. electrolytically or by vapor deposition, a thin (less than 1 micrometer) film of platinum. The invention allegedly avoids the problems associated with the immobilisation of the enzyme directly onto the platinum surface.

UK patent application No. 2,191,003 A discloses the improvement of the electrode as disclosed in the above Japanese patent publication No. 81-163447. This enzyme electrode comprises the enzyme immobilized or adsorbed on the surface of an electrically conductive support member (platinised carbon paper available under the name "Prototech" from Prototech Co. and platinised carbon powder particles [Vulcan XC-72] integrated body), which comprises a porous layer of resin-bonded carbon or graphite particles, the particles having intimately mixed therewith, or deposited or adsorbed onto the surface of the individual particles prior to bonding to form the layer, a finely divided platinum group metal. The response of the electrode is significantly slow, because it takes some period to stabilize the response current. The sensitivity for the measurement of the glucose concentration is in order of milli Mole, and significantly lower than that of our electrode (in order of micro Mole.)

In those prior art electrodes, the electrodic reaction and enzymatic reaction are carried out in separate places. In the other words, the electrode and the media in which the enzymatic reaction takes place or occurs are separated, and therefore, are not integrated. Therefore, the high speed measurement cannot be expected, and the miniaturization of the device is difficult.

SUMMARY OF THE INVENTION

With the foregoing considerations in mind, the present invention contemplates the provision of a microbioelectrode and the method for preparation of the same. Such microbioelectrode can be assembled in new sensing device to determine physiologically active substance.

It is an object of the present invention to provide an efficient microbioelectrode with high speed responsitivity and high sensitivity and a method for the preparation of the same by one step process.

It is an another object of the present invention to provide a new type of an electrode structure which can be miniaturized to the micrometer order, and can function as a highly sensitive electrode to detect physiologically active substances which can be recognized with a biologically active substance, which is maintained in the microbioelectrode.

It is a further object of the present invention to provide a new method of preparing an sensitive, miniaturized electrode with rapid detection of a physiologically active substance.

Throughout the specification, the below listed terms are used to mean the following terminology.

"Transducing electrode" means "an electrode where enzyme-generated or physiologically generated electrochemically active species is converted to generate an electric signal".

"Enzyme-embodied electrode" means "a porous transducing electrode in which enzyme molecules or biologically active substances are directly immobilized, consequently a biochemical reaction and an electrochemical reaction can occur simultaneously therein".

"Microbioelectrode" prepared in accordance with the present invention means "an electrode having a diameter to the level of micrometer order, preferably in the range from 1 micrometer to several millimeters, which has porous conductive layer incorporating 'biologically active substance(s)' immobilized therein".

"Biologically active substances" means "substances to be immobilized or incorporated in a porous conductive layer formed on the minute surface of a transducing electrode employed for the fabrication of the microbioelectrode of the present invention". "Biologically active substance" may include enzyme, antibody, antigen, organelle, various catalyst, microorganism, and binding protein. "Physiologically active substances" may include "intermediate metabolites, hormonic substances and tumor-related markers, which can be determined by the inventive microbioelectrode" through a reaction with the above-mentioned "biologically active substances".

DETAILED DESCRIPTION OF PREFERRED EMBODIMENTS

Figure 1A:
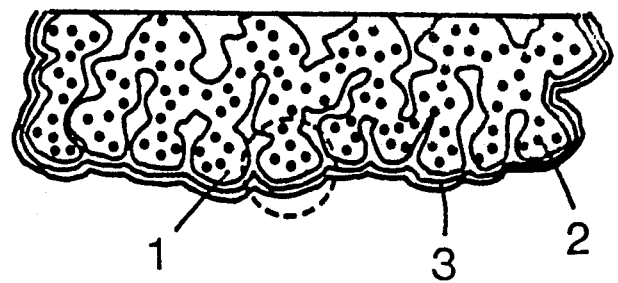
FIGS. 1A and 1B show schematically a sectional view of the microbioelectrode prepared by the present invention, and the magnified view of the encircled portion, showing detailed structure of porous conductive layer in which enzymes are incorporated and immobilized.

The inventors have found that a biologically active substances can be immobilized in the interior or on the surface of porous conductive material layer or fine particle conductive layer on a surface of a conductive material by a single step of depositing electrochemically very fine conductive particles or porous conductive layer on the surface of a transducing material, from a solution containing a precursor of conductive material as dissolved, and a biological active substances.

Further, the process for production of the inventive microbioelectrode may comprise alternatively further stabilizing the incorporated biologically active substance(s) with a crosslinking agent.

In the method of fabrication of the inventive microbioelectrode, the conductive material to be used as transducer matrix, that is, the conductive material of the layer is not necessarily the same as the base conductive material for the electrode.

For example, the combination of platinized platinum (platinum black) on the surface, e.g. of the edge of a platinum wire can be preferably used wherein the platinized platinum or platinum black is deposited on the surface by treating electrolytically the surface of the platinum in a solution containing a platinum complex and a biologically active substance. The other porous conductive material such as gold black, particulate rhodium oxide or particulate ruthenium oxide ($RuO_3$), palladium black, or iridium black can be used to be deposited or formed in place of the platinum black on the surface of the edge of a platinum wire so as to produce the inventive microbioelectrode. Any materials which can form conductive layer of fine particle material on a conductive surface of a base for the electrode can be used unless no troubles can be found.

Further, the other conductive material such as gold wire, silver wire and the other metal wire can be used as a base transducing material for the inventive microbioelectrode in place of the platinum wire.

Because such conductive porous layer can be formed on the minute surface of the conductive base as mentioned above, the inventive microbioelectrode can have surface area of several thousands times greater than that of the apparent surface area, and then, has high selectivity to the substance(s) to be detected, with high S/N ratio due to the sufficient amount of immobilized enzyme within the porous electrode matrix (layer) of the inventive microbioelectrode.

This high S/N ratio of the measured value, measured by the application of potential to the inventive microbioelectrode, meets the requirement of high sensitivity to the physiologically active substance to be detected, with a wider dynamic range. The inventive microbioelectrode can demonstrate sufficient output even if the sensor using this electrode can be in very small size, because the actual surface area thereof is much higher than what is expected from its apparent size. Therefore, the amount of the sample required for the measurement of the response output can be very small, and the analytical apparatus using the inventive microbioelectrode can be easily miniaturized, i.e. the desired microinstrumentation can be easily carried out. The advantages of the analytical apparatus being in small size are supported in a batch system measurement as well as in a flow injection analysis. Further, the analytical apparatus using the inventive microbioelectrode is advantageous in rapid response, high sensitivity and high resolution with wide dynamic range. Further, the inventive microbioelectrode can be used and assembled in a rapid biosensing device which can detect a target substance within a few milliseconds even when using trace droplet samples.

It has been known that an electrode with platinized platinum having very high surface area can have high catalytic activity for hydrogenation. However, the incorporation or immobilization of biologically active substance(s) in such platinized platinum layer has not been known.

While there has been known the immobilization of enzyme and the like in the pores of platinum, which pores are fabricated by etching, and then bind the enzymes on the surface of the platinum with a crosslinking agent, those porous surfaces have only several $m^2/g$ of surface area in an ordinary condition, for example, as disclosed in Japanese Laid-open Patent Application No. 57-107,764. However, it has been unknown that the size of platinized platinum pores can be controlled so as to incorporate the biologically active substance(s) in the pores.

In accordance with the present invention, the biologically active substances can be immobilized or directly unitized among the fine porous particles of an electrically conductive material, so as to fabricate a new type bioelectrode having incorporated therein biologically active substance(s) on or among the fine porous particles of the conductive material.

This can be performed, for example, by depositing fine particles of an conductive material on the surface of an electroconductive material from a solution containing the conductive material or a material to generate the conductive material by a chemical reaction, and said active substance so as to form a porous conductive material (or conductive fine particle layer) incorporating said active substance therewithin.

The process of preparation of the microbioelectrode may comprise further stabilizing the immobilized active substance with a polymeric material such as albumin or heparin so as to prevent any trace dissolution of the active substance from the conductive porous layer. Further, the immobilized substance can be insoluble with a crosslinking agent so as to form an insoluble crosslinked substance on the conductive porous layer. Therefore, the method of immobilizing the biologically active substance on or among the fine particles of the conductive layer in accordance with the present invention can be applied to the whole immobilization of enzymes in a molecular form.

Further, a film can be formed on the active substance immobilized layer in the thickness of several thousands Angstrom or less, and therefore, the presence of the film does not affect the activity of the immobilized biologically active substance incorporated in the porous conductive layer.

Polymeric material(s) which can be used for covering the surface of the microbioelectrode in accordance with the present invention may include proteins such as albumin, and polysaccharides such as heparin.

The usable crosslinking agent in accordance with the present invention is preferably a crosslinking agent adopted for the biologically active substance. The usable crosslinking agent may include glutaraldehyde, carbodiimide and maleinimide coupling agents.

Further, an electron mediator such as ferrocene can be incorporated in the fine particle conductive layer with a biologically active substance, so as to enable measuring a target determinant even in the absence of dissolved oxygen or with less oxygen, otherwise oxygen has to be dissolved in a solution containing a target analyte. Further, the presence of mediator in the porous conductive layer enables to reduce significantly the potential necessary for the measurement of the target substance by using the inventive microbioelectrode. Such further treatment of the microbioelectrode with mediator may reduce the influence of concomitant oxidizable substances such as ascorbate and uricate.

Figure 1B:
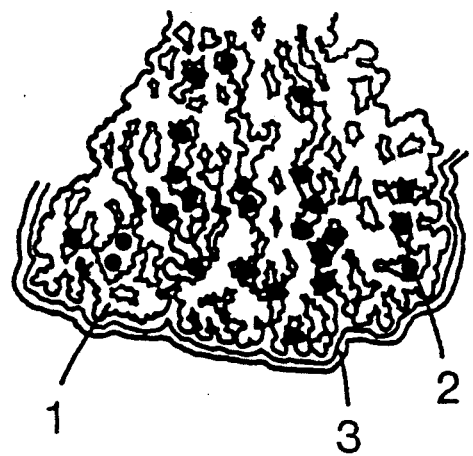

The structure of the conductive porous layer formed on the conductive base in accordance with the present invention is shown in FIGS. 1A and 1B, showing the incorporation of biologically active substance immobilized therein. As shown in the drawings, the active substance is incorporated on or among the conductive fine particles in the layer. For example, the platinum fine particles (platinum black) layer, as deposited electrically on the surface of an electrode base, and incorporating the active substance among the particles can not be easily peeled off even when the microbioelectrode is vigorously agitated in a solution, and maintains the activity of the incorporated and immobilized biologically active substance such as enzyme. The active substance can be crosslinked so as to stabilize the active substance in the pores of the layer. Further, the enzyme-incorporated platinum black layer can be coated with polymeric material such as albumin.

Recently, Polta and Johnson have proposed the electrochemical determination of electro-inactive species in the article in Analytical Chemistry, 59, at pages 204 to 207 (1985). They employed the formation of surface oxide on the surface of a metal electrode for the determination of carbohydrates and amino acids. In their proposal, non-specific response to the determinant was utilized.

In contrast, in the microbioelectrode of the present invention, the selectivity on the measurement of a target can be improved by anodically polarizing the microbioelectrode.

An analytical instrument which can be fabricated by using the inventive microbioelectrode will be developed in a miniaturized size but have rapid response and high sensitivity. This feature is extremely important for the development of a clinical analyzer or a downstream analyzer that requires miniaturization of a biosensor with multiple functions.

The inventive method of immobilizing an active substance in an electrode will develop a special electrode which are characterized by whole incorporation of active substance such as enzyme and antibody without any affection to the active substance due to intact immobilization.

The inventive microbioelectrode provides; 1) highly sensitive detection, 2) rapid response, 3) sufficiently long life time and 4) reliable reproducibility. Such high performance of an electrode can be afforded mainly from the high density of immobilized active substance in the very fine particles (platinum black) in the deposited layer formed on the surface of conductive material.

The inventive microbioelectrode is advantageous in low S/N ratio, because it has very large surface area amounting to much higher orders of the magnitude than the apparent surface area, which can be fabricated by the deposition of conductive fine particles on the flat surface of a conductive base.

An analytical instrument which can be manufactured by using the inventive microbioelectrode will evidence high performance such as highly rapid response and high sensitivity, which can be found preferably in both of batch analysis and flow injection analysis. Further, the inventive technique will provide a biological analytical system with high resolution and stability, because the inventive microbioelectrode incorporates stably a biologically active substance therein.

In the batch system measurement, a linearity between generated current (or the current height at the certain time after the initiation of potential application) and concentration of a target substance (or glucose for example) is found or can be established in the range from 0.5 micro moles (mol/l) to 50 mM (millimoles). Because the present invention employs electrochemical technique and the inventive microbioelectrode is fabricated by the deposition of conductive fine particles or conductive porous layer, the inventive microbioelectrode may be in any form, and preferably, in disc, spherical or tubular form. Further, the inventive microbioelectrode can be in very small size, and therefore, the sample to be measured can be in an extremely small amount even for the measurement of a target substance in very low concentration. Further, very high speed measurement can be enabled, i.e., several hundred samples per one hour can be dealt in a continuous flow measurement.

The inventive microbioelectrode can be assembled in an array, which facilitates multifunctional measurement of multiple components in one sample at the same time in a flow analysis or in a batch analysis.

Figure 9:
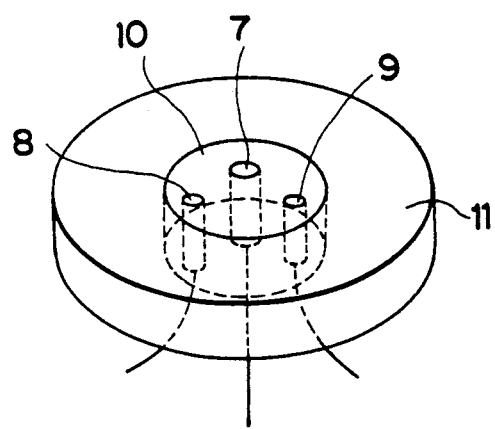
FIG. 9 shows a schematic view of a planar sensing cell using the inventive microbioelectrode 7 with three electrode measurement system, where pulse voltammetric potential is applied to the microelectrode as a working electrode.

One of the biosensor using the inventive microbioelectrode can be a real time measuring device which has three electrodes including the inventive electrode assembled in a small size device, and therefore, can be operated by a pulse potential application mode. Then, droplet stationary samples can be loaded on the sensing device using the inventive microbioelectrode. The output generated in the sensor by using the microbioelectrode is taken in a few milliseconds for the measurement of a target substance, e.g. droplet samples containing glucose is loaded on the sensing device where a glucose oxidase immobilized microbioelectrode in accordance with the present invention, a counter electrode and an Ag/AgCl reference electrode are assembled on a tip of a Teflon casing as shown in FIG. 9.

The inventive microbioelectrode can be used so as to enable measuring a very small amount of samples, e.g. a droplet sample of only one microliter.

After a very small amount of sample is loaded, a potential is applied to the electrode, and the generated current thereby is detected, and then, the concentration of the target substance in the sample can be determined from the height of the current.

The active substance (e.g. glucose oxidase) incorporated in the porous layer of the inventive microbioelectrode will react with a target substance (e.g. glucose) by applying a potential to the electrode, so as to oxidize (or reduce) an enzymatically generated electroactive species at the electrode, thereby generating a current in the electrode, which current can be detected by a recorder. Therefore, the current can be detected in real time by pulse voltammetric mode.

Various pulse application modes can be used to detect the current using the inventive microbioelectrode, and further a sample can be measured even in a stationary state. Because the bioanalytical system using the inventive microbioelectrode can detect directly the active species generated in the electrode, any of bioactive substances, such as oxidizing enzymes and dehydrogenating enzymes can be employed as a biologically active substance in the conductive porous layer of the electrode.

The inventive method of immobilizing a biologically active substance in the porous layer of the electrode can provide unique enzyme electrodes such as the ones described herein. An analytical system or method for measurement with microbioelectrode is advantageous in high performance such as rapid response and high sensitivity, and further, can provide an in vivo biosensing system and a portable biosensor, and can be further applied to a potentiometry-based biosensor.

BEST MODE FOR CARRYING OUT THE INVENTION

In carrying out the present invention, three modes of applying immobilized biologically active substance(s) by using the inventive microbioelectrode are illustrated. In describing these modes, glucose oxidase is taken as a typical example of a biologically active substance to be immobilized in the porous conductive layer, and glucose is to be determined by the inventive microbioelectrode.

A transducer base to be used for the formation of very fine particle layer or porous conductive layer on its surface can be platinum wire having a diameter below one milimeter, and further, the size in the order of micrometer can be produced. The fine particle layer or porous conductive layer is formed by electrolytically depositing the conductive material (e.g. platinum black) on the surface from a solution containing a platinum complex, and a biologically active substance, e.g. a desired enzyme and preferably further a trace amount of lead ion for smooth deposition of platinum black. The fine particles conductive layer incorporating a biologically active substance, e.g. enzyme, can be prepared by depositing fine particles of an conductive material on the surface of an electroconductive material from a solution containing a conductive material or a material to generate the conductive material by a chemical reaction, and said active substance so as to form a porous conductive material (or conductive fine particle layer) incorporating said active substance therewithin. Further, the enzyme molecules within the layer can be crosslinked by a bifunctional coupling agent, to ensure stable immobilization of the enzyme thereby, enabling to have long lifetime of the resulting microbioelectrode of the present invention.

Any of the electrically conductive materials such as metal, carbon and conductive polymer can be used as a base conductive material for the inventive microbioelectrode. Suitable material for the base of the electrode may be metallic substance such as platinum, gold, graphite. When the material for the base is metal, suitable form is preferably wire, or pin.

Porous layer or very fine particle layer can be prepared on the surface of the base material. The material of the layer is electrically conductive and preferably is a particular porous layer which can be electrochemically deposited on the surface of the conductive material, so as to form such fine particle layer or porous layer.

Suitable material for the layer may include platinum black, gold black, palladium black, iridium black, rhodium oxide, ruthenium oxide ($RuO_3$), conductive polymer and graphite.

Either potentiostatic or galvanostatic deposition of conductive fine particles can be used to form such layer on the surface of the conductive base. Potential and current requirements are dependent on the metal complex and geometrical parameters of the base for the electrode. Generally speaking, it is preferable to use a relatively low voltage supply for deposition of conductive particle layer, in the case of potentiostatic deposition, such as from about minus 0.1 to minus 0.2 volts versus an Ag/AgCl electrode. When galvanostatic deposition is used to form the layer, one should pay attention to the drastic change in pH in the vicinity of the electrode because hydrogen gas is generated from the surface of the electrode. The time required for immobilizing enzyme in the micropores of the layer is mainly dependent on the enzyme concentration in the solution for deposition of the layer.

Referring now to FIGS. 1 A and 1 B, a porous layer 1 of conductive material, or a layer of conductive and very fine particle is electrochemically formed or deposited on the surface in very small size of conductive material base, and further, a thin polymer film 3 is formed on the surface of the porous transducer matrix 1 (or the layer 1) of the electrode. Further, enzyme 2 can be stabilized chemically.

The enzyme electrode (microbioelectrode), a counter electrode and a reference electrode are immersed in a solution to be measured, and followed by applying a potential of 0.6 V versus the Ag/AgCl reference electrode. As soon as the background current reaches to a steady state current, a glucose sample is added. The current generated upon the addition of glucose is a sensor response in a batch system measurement.

Figure 4:
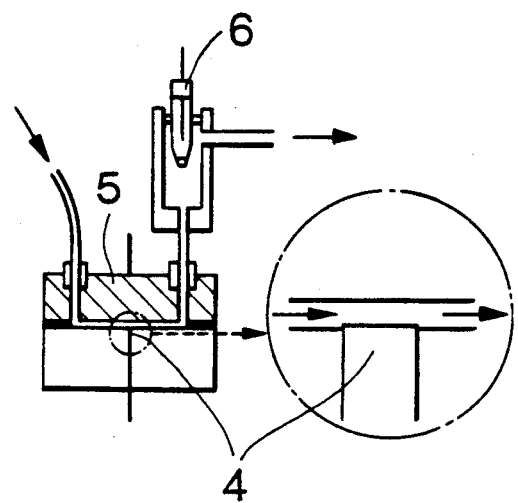
FIG. 4 shows schematically the structure of a electrode assembly transducing cell using the inventive microbioelectrode 4 as a detector, for a flow injection analysis.

An electrode assembly for flow measurement is shown in FIG. 4, wherein an electrode 4 of the present invention is assembled in a thin layer cell along the passage flow of the sample, and a stainless steel upper cell 5 acting as a counter electrode is assembled as shown in the drawings, and an Ag/AgCl electrode 6 is positioned at the downstream along the passage flow of the sample. A glucose sample can be repeatedly injected to a mobile buffer to pass through the passage flow.

The other type of an electrode assembly for measurement by the application of voltammetric pulse is shown in FIG. 9. An electrode 7 of the present invention, a counter electrode 9 and an Ag/AgCl reference electrode 8 are assembled into a biological sensing device, wherein a trace droplet sample is loaded for the pulse voltammetric or chronoamperometric measurement.

In addition, anodic polarization treatment of the resulting microbioelectrode can enable to improve the selectivity to a physiologically active substance or a target substance. In other words, formation of surface oxide on the microbioelectrode makes the sensor reliable selectivity, as the electrode surface becomes inactive in nonspecific adsorption of ingredients. The anodic polarization treatment is to form surface oxide at the electrode for its inactivation.

The present invention is illustrated in detail by the following examples, but should not be interpreted for the limitation of the invention.

EXAMPLE 1

Fabrication of a Biologically Active Substance Immobilized Electrode (Microelectrode)

A platinum wire having a diameter of 50 microns was sealed in a soda glass tubing, and the end surface of the wire was polished with alumina powder to form a clean, flat end surface for a platinum electrode. The resulting surface was electrochemically cleaned for 30 minutes in a bath of 0.5 Molar sulfuric acid solution, using a silver/silver chloride electrode as a reference electrode. The potential applied to the platinum electrode was scanned between 1.3 V and minus 0.25 V at a scanning rate of 100 mV/sec.

The immobilization of enzyme was carried out by the following two different ways.

(A) Electrolysis was carried out in a solution of sodium sulfate having 0.2 mole/liter and pH of 3.2, containing hexachloroplatinate (1 mg/ml) and glucose oxidase (1 mg/ml), using silver/silver chloride electrode as a reference electrode, and the platinum wire which had been prepared as above, as a functional electrode, by applying a constant potential at minus 0.2 volt, for ten minutes, to form a deposit of platinum black incorporating the glucose oxidase.

(B) Electrolysis was carried out in a solution of sodium sulfate having 0.2 mole/liter and pH of 3.5, containing hexachloroplatinate (33 mg/ml), lead acetate (0.6 mg/ml) and glucose oxidase (10 mg/ml), using silver/silver chloride electrode as a reference electrode, and the platinum wire which had been prepared as above, as a functional electrode, by applying a constant current of 5 microampere, for ten minutes, to form a deposit of platinum black incorporating the glucose oxidase. The formed platinum black layer was about several micrometer thick.

Then, the resulting platinum black electrode was dried at 25° C. for 60 seconds by blowing air, and the electrode with an immobilized glucose oxidase was washed overnight in a 0.1M buffer solution of phosphoric acid (pH=7.0), and tested for the measurement of glucose concentration.

In the preparation of the microbioelectrode as mentioned above in accordance with the present invention, glucose oxidase having isoelectric point of 4.2 and therefore positively charged was deposited on the surface of the platinum black precipitated, and as the result, the enzyme was immobilized in the pores of the platinum black fine particles, as shown in FIGS. 1A and 1B.

Enzyme can be immobilized by any of the above two processes (A) and (B). The adjustment of the fixed enzyme amount can be rather effected by the process (A), because the enzyme being positively charged is deposited in a negative potential range, and the platinum black can grow at a constant potential. Then, in the process (B) wherein the deposit is formed by applying a constant current, the potential will be changed to decrease gradually a current density, as the platinum black layer grows. Therefore, in the process (B), the time for the preparation is longer, and it will be more difficult to form a homogeneous deposit.

Alternatively, for the stable immobilization of the the immobilized bioactive substances, the porous layer is further immersed for another 10 minutes in one mililiter of phosphoric buffer solution containing 10% of albumin, and then treated with the bifunctional agent to prepare an albumin thin film over the surface of the porous layer.

The response property of the resulting electrode of the present invention was evaluated in an electrochemical cell containing a buffer solution of phosphoric acid, where a reference electrode, a counter electrode and the microbioelectrode as a working electrode were employed in a three electrode system.

Each of those electrodes was connected respectively to a potentiostat. A potential of 0.6 volt was applied to the microbioelectrode versus the reference electrode, and then, glucose was added, and the resulting oxidation current was measured.

Figure 2:
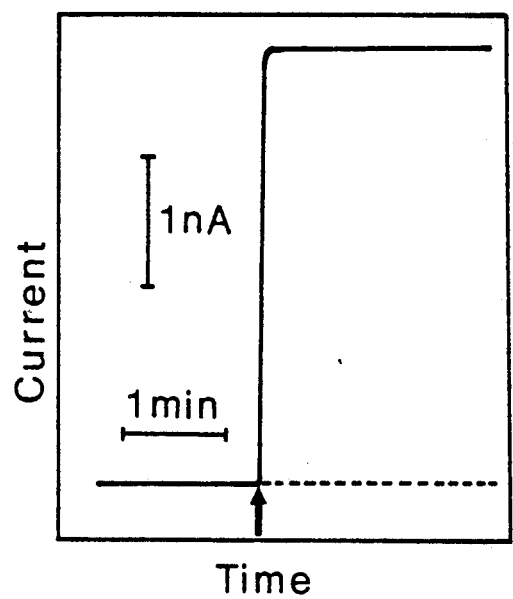
FIG. 2 shows a response curve measured by using the inventive microbioelectrode incorporating glucose oxidase in a batch system measurement, when a glucose sample is injected at the time shown by an arrow, wherein the electrode potential is 0.6 V versus Ag/AgCl electrode.
Figure 3:
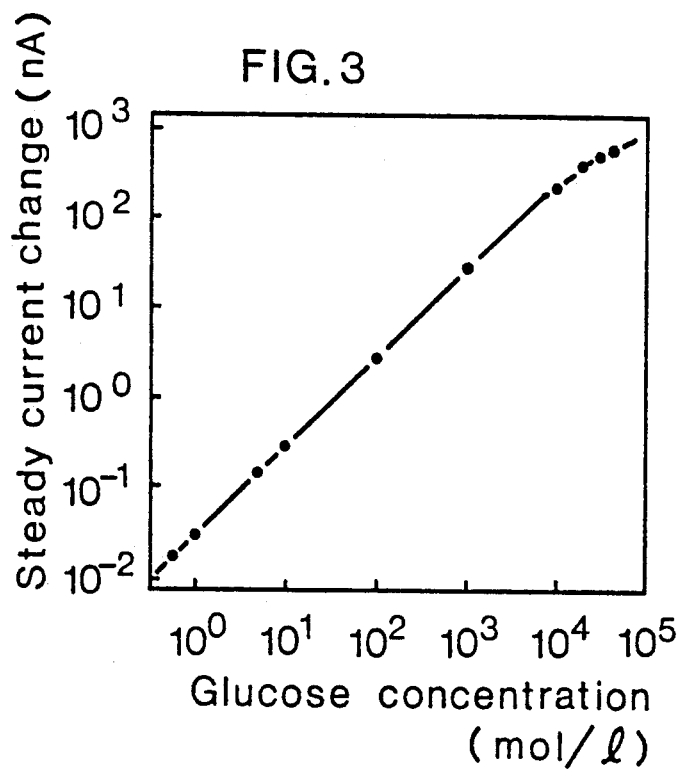
FIG. 3 shows the relation between microbioelectrode output (steady current change in nano ampere: plotted on the ordinate) and glucose concentration (mol/liter) measured by using the inventive microbioelectrode having glucose oxidase, in a batch system measurement, wherein a potential of 0.6 V versus Ag/AgCl electrode is applied to the electrode.

The microelectrode showed 100% response within three seconds (FIG. 2). As shown in FIG. 3, it evidences that the inventive microbioelectrode can measure even in the order of 0.1 mg/dl, and the current increases linearly at a concentration range from 0.1 mg/dl to 100 mg/dl.

EXAMPLE 2

Relation between the size of Electrode and the Sensitivity.

The process (A) of potentiostatic deposition was used to prepare the microbioelectrode in accordance with the present invention. The potential for platinum deposition was minus 0.17 volts versus the reference electrode. The deposition period for immobilization was 5 minutes in every microbioelectrode.

The microbioelectrodes of various sizes were fabricated. Then, the fabricated microbioelectrodes were evaluated in terms of responsiveness, response ability and detectable range. The result is shown in Table 1.

TABLE 1

| Fabrication Condition | | Characteristics of Electrode | | | |
|---|---|---|---|---|---|
| Electrode Size (micrometer) (diameter) | Peak height of wave (microampere) | Response to mM (nA) | Detectable Range (M) | (mM) | KCV (N) % |
| 1 | 1 | 0.6 | $10^{-4}$–$10^{-2}$ | 80 | 4.0 (10) |
| 10 | 8 | 5.5 | $10^{-5}$–$5 \times 10^{-2}$ | 60 | 2.0 (10) |
| 50 | 22 | 31.0 | $5 \times 10^{-7}$–$10^{-2}$ | 45 | 1.5 (20) |

TABLE 1-continued

| Fabrication Condition | | Characteristics of Electrode | | | |
|---|---|---|---|---|---|
| Electrode Size (micrometer) (diameter) | Peak height of wave (microampere) | Response to mM (nA) | Detectable Range (M) | (mM) | KCV (N) % |
| 200 | 69 | 180 | $5 \times 10^{-7}$–$10^{-2}$ | 35 | 1.0 (20) |
| 500 | 120 | 290 | $5 \times 10^{-7}$–$10^{-2}$ | 30 | 0.7 (20) |

The first column indicates the size of the electrode in micrometer, i.e. the diameter of platinum wire. The second column indicates the peak height of $H_2$ adsorption wave by a cyclic voltammetry in microampere. The third column indicates one of the properties of the fabricated microbioelectrode, the mean response to 1 mM glucose in nano-ampere. The forth column indicates the detectable range of the concentration of glucose in molar. The fifth column indicates Michael's constant, Km in unit of mM. The last column indicates the coefficient of variation (%) in glucose response determination.

Using the fabrication condition shown in Table 1, the glucose oxidase incorporated platinated platinum layers were deposited on the edge surface of platinum wires having the sizes (diameter) as shown in Table 1, for 5 minutes in every electrode, and then, the sensitivity and the dynamic range were measured as shown in Table 1.

In the above-mentioned preparation of the microbioelectrode of the present invention, the potentiostatic deposition of conductive fine particles was used to form such layer on the surface of the conductive base. The galvanostatic deposition can be alternatively used.

EXAMPLE 3

Flow Injection Analysis using Microbioelectrode

Figure 7:
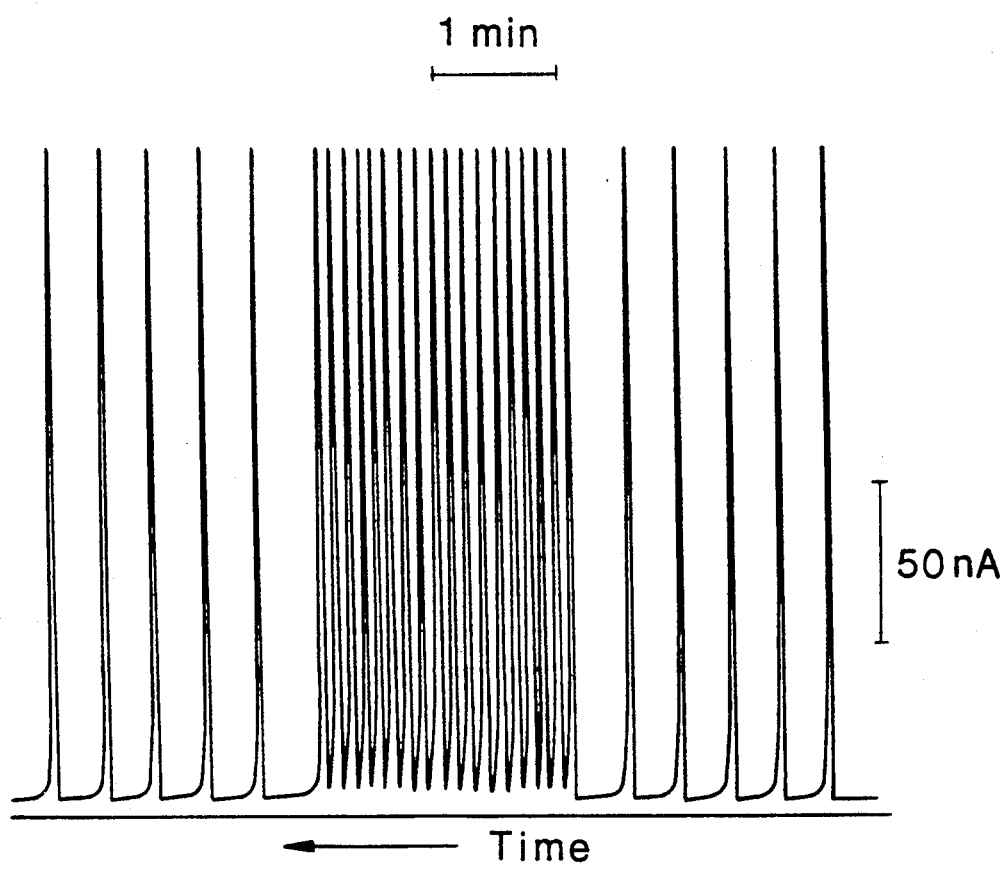
FIG. 7 is a graph showing repeated response measured by using the microbioelectrode in a flow injection measurement.

The microbioelectrode having a diameter of 100 micrometer was assembled in a thin-layer transducer cell (FIG. 4) for a flow injection analysis, and was used to measure the peak height current corresponding to the known concentration of glucose. The typical response are shown in FIG. 7. Approximately 10 samples were injected in an interval of about one minute to the flow injection analysis.

Figure 6:
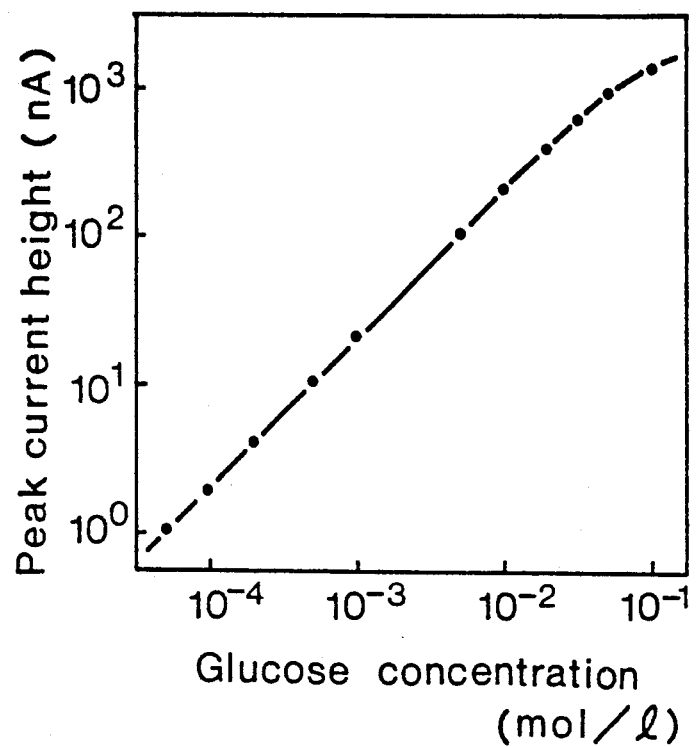
FIG. 6 is a graph showing the relation between glucose concentration (in mol/liter, as plotted on the abscissas) and response output (in nano ampere, as plotted on the ordinate) measured by using the inventive microbioelectrode in a flow injection measurement.

A series of glucose samples were prepared and injected into the assembled cell for the flow injection analysis, and then the peak current was measured. The resulting peak height was plotted to the glucose concentration as shown in FIG. 6.

An aliquot of glucose sample (10 microliter) containing 10 mM glucose was repeatedly injected to the assembly of FIG. 4 using the inventive microbioelectrode, so as to determine coefficient of variation in the flow injection measurement. Six hundred samples could be injected in one hour, and then the current generated could be measured.

The coefficient of variation for 600 samples was less than one percent. Excellent coefficient of variation was obtained by the assembly of FIG. 4, using the inventive microbioelectrode.

EXAMPLE 4

Relation between Electrode Size and Response Time

A variety of the microbioelectrodes were assembled in a thin-layer transducer cells as illustrated in FIG. 4.

Figure 5:
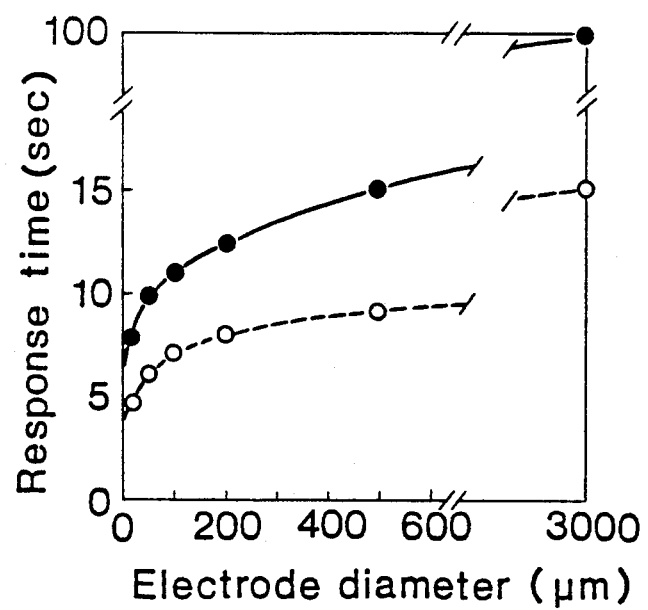
FIG. 5 shows the relation between the response time (in seconds, as plotted on the ordinate) and the diameters (in micrometers, as plotted on the abscissas) of the inventive microbioelectrode in measuring response current in a flow measurement of a glucose containing solution.

FIG. 5 shows the relation between the electrode size and the response time. The solid line indicates a time necessary to return to the base current. The broken line denotes a shortest time that succesive and intermittent injections do not interfere with each other as shown in FIG. 5. It is apparent that one of the advantages is the smallness of the electrode, i.e. the smaller the electrode, the faster the response.

EXAMPLE 5

Life time and Stability of Microbioelectrode

Figure 8:
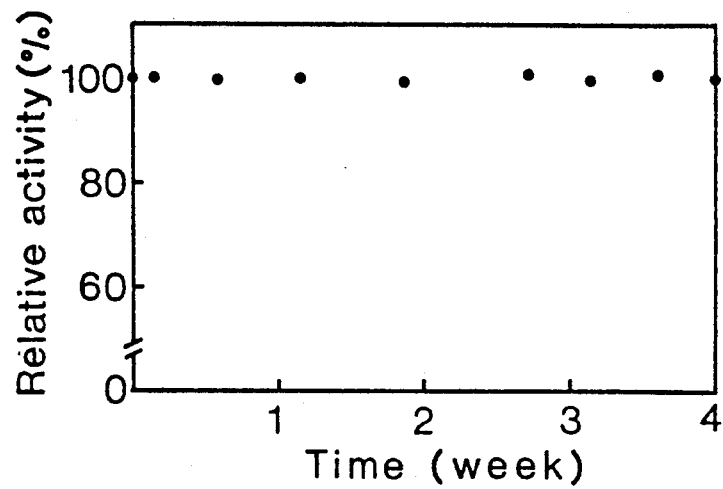
FIG. 8 is a graph showing the time stability of the current value measured by using the inventive microbioelectrode in a flow injection measurement, where one hundred samples are injected in each point.

The measurement of glucose sample was continued for one month by injecting samples repeatedly to the assembly of FIG. 4. The response was recorded, and the result is shown in FIG. 8. Each point represents one hundred samples injected at room temperature. This assembly was stored in a refrigerator when not in use.

EXAMPLE 6

Microbioelectrode for Transient Response Mode Analysis

The inventive microbioelectrode 8 having a diameter of 50 micrometer, a counter electrode 9 and an Ag/AgCl reference electrode 7 were assembled in a biosensing device as shown in FIG. 9.

Figure 10:
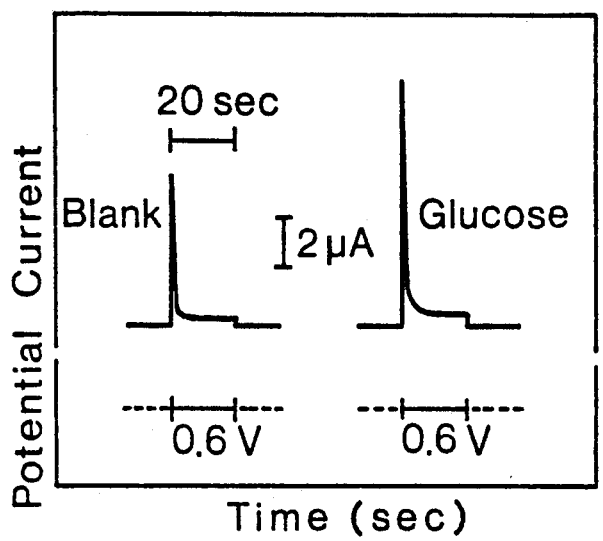
FIG. 10 is a graph showing the current (the upper portion of the graph) generated when the constant potential (the lower portion of the graph) is applied to the sensing device using the inventive microbioelectrode as shown in FIG. 9, wherein the response current curves were measured by an X,t-recorder with response time of 200 milliseconds.

After loading a droplet (10 microliter) of sample containing 10 mM of glucose, a potential of 0.6 V versus Ag/AgCl reference electrode was applied to the device by a potentiostat. The transient output of the biosensing device was recorded with an X-t recorder of 200 milliseconds response time. A phosphate buffer solution of 0.1M was taken as a blank sample. The response curves for a blank sample and a glucose sample were shown in FIG. 10.

Figure 11:
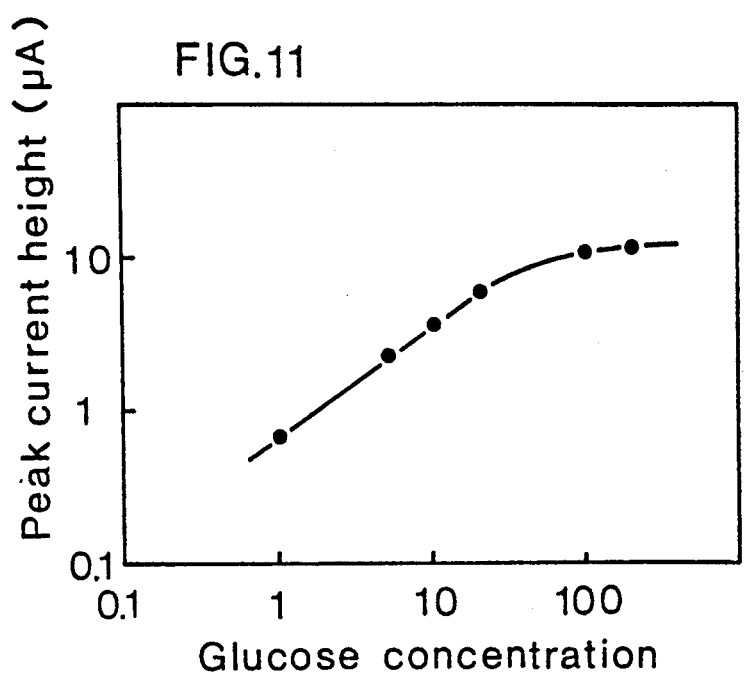
FIG. 11 is a graph showing the relation between the current (in microampere, as plotted on the ordinate) generated by the inventive microbioelectrode and the glucose concentration (in mol/liter, as plotted on the abscissa), as measured in the sensor of FIG. 9.

Next, a series of samples having different glucose concentrations were loaded on the device of FIG. 9 to measure the output response current. The differences between the peak current for the predetermined glucose concentration and that for a blank were plotted in a graph of FIG. 11.

EXAMPLE 7

Dependence of Transient Response on Sample Volume

Figure 12:
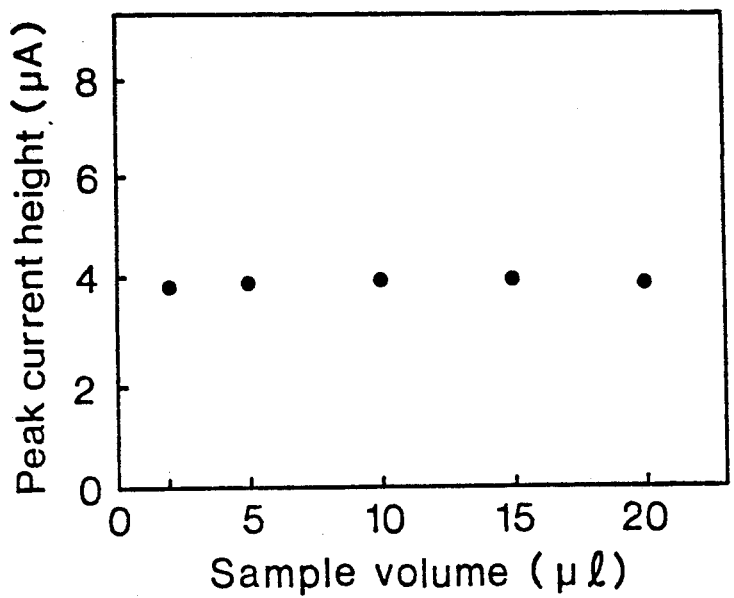
FIG. 12 is a graph showing the relation between the sample volume (in microliter, as plotted on the abscissa) to be determined, and the peak current (in microampere, as plotted on the ordinate) measured by using the inventive microbioelectrode with the device as shown in FIG. 9.

A series of glucose droplets of 10 mM samples having different volume were loaded on the device of FIG. 9 to measure transient response current. The difference in peak height between glucose concentration and a blank was shown in FIG. 12. This result shows the advantage of the present biosensing device using the inventive microbioelectrode, over the conventional apparatuses, which require additional attachments such as a mixer and/or a pipetting machine.

EXAMPLE 8

Detailed Study on the Transient Response

A transient memory of 12 bit $\times$ 4096 words was used to read and record the very rapid response signal generated by the inventive microbioelectrode.

Figure 13:
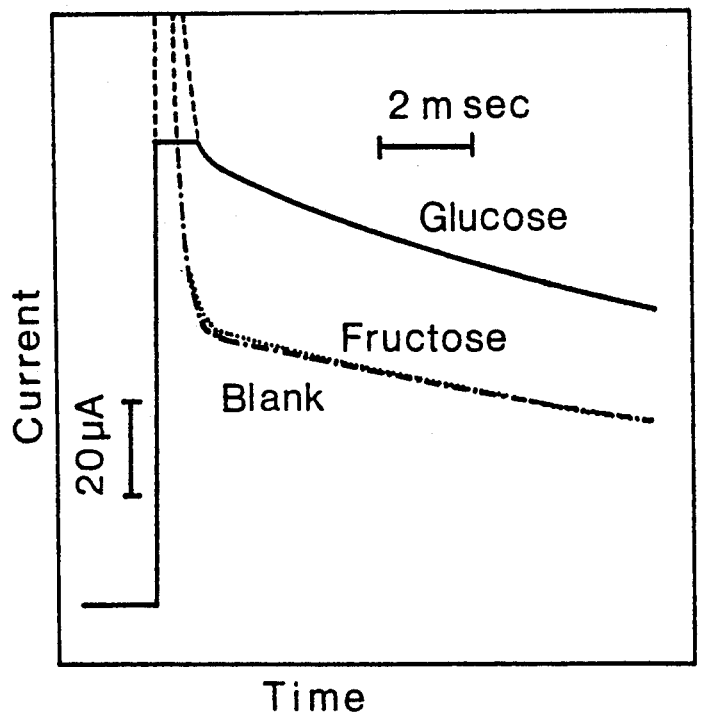
FIG. 13 is a graph showing closely a transient response as generated by the inventive microbioelectrode in the sensor of FIG. 9, where the response curves were measured by a transient memory.

The transient response upon the application of 0.6 volt versus Ag/AgCl reference electrode was recorded for glucose (20 mM), fructose (20 mM) and blank samples. Every response is shown in FIG. 13, which behaves a typical response caused by potential-application, i.e. the steep decay of charging current is followed by the gradual decrease of faradaic current. After the sufficient decay of capacitive (charging) current, the faradaic current was taken as a biosensing signal, i.e. after the rapid decay of the capacitive current, the faradaic current for hydrogen peroxide remained.

EXAMPLE 9

Measurement of Concentration by Transient Response Current

Figure 14:
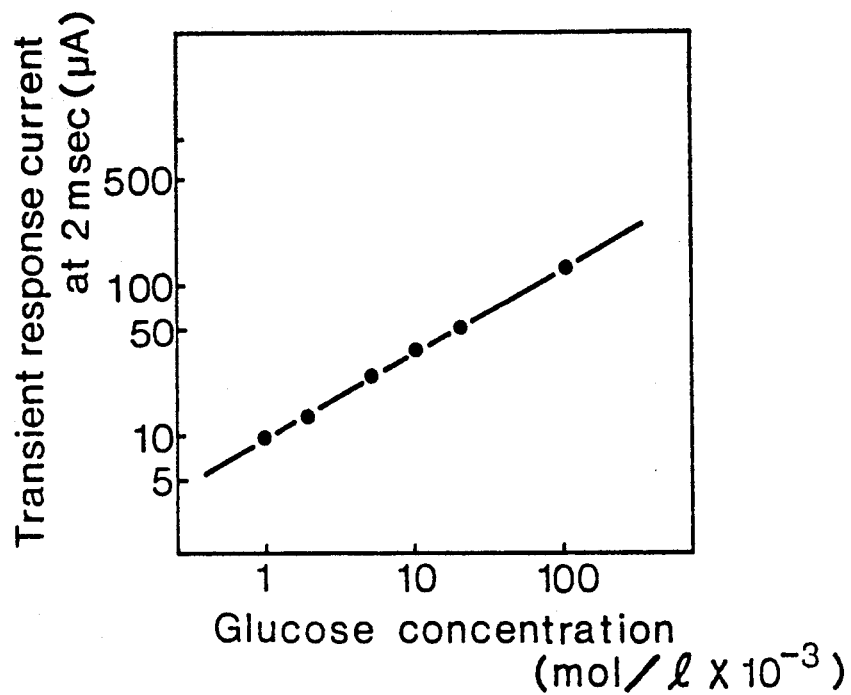
FIG. 14 is a graph showing the relation between the glucose concentration (in millimole/liter, as plotted on the abscissa) and the sensor output (in microampere, as plotted on the ordinate) (of which transient response was measured at 2 milli seconds after the potential application), where the sensor output herein as plotted was the difference between the response current for a glucose containing sample and that for a blank sample.

The difference in output current between a glucose sample and a blank sample at the time of 2 microseconds after the application of a potential to the microelectrode versus the Ag/AgCl electrode was measured and plotted against the glucose concentration in a graph of FIG. 14.

A good linearity between the transient response and the glucose concentration is shown in FIG. 14.

Figure 15:
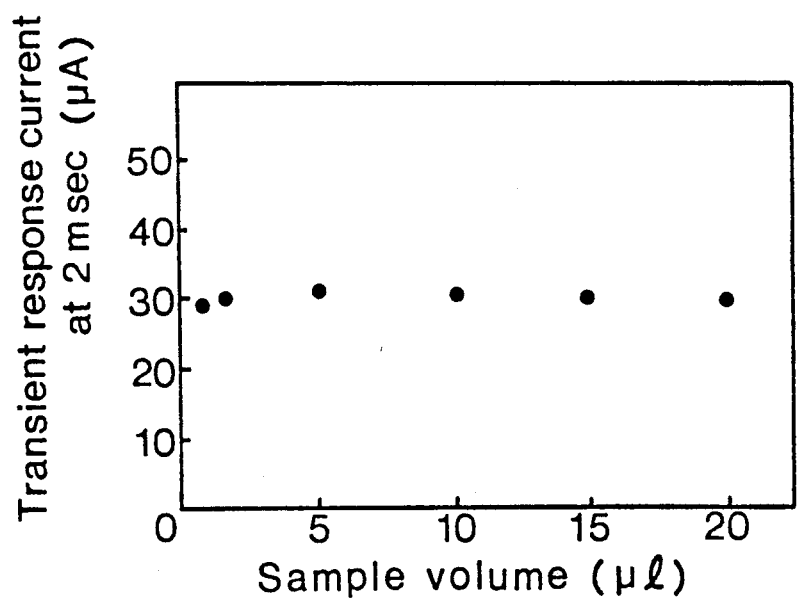
FIG. 15 is a graph showing the relation between the volume of the glucose containing sample and the sensor output (in microampere, as plotted on the ordinate) measured at 2 milli seconds after the potential application.

The response current was measured by changing the volume of the sample using the inventive microbioelectrode. The result is shown in FIG. 15. The coefficient of variation of the measured current was within 4% when n=10. It is revealed that the response current generated by the reaction in the biosensing device is independent of the sample volume to be loaded for the measurement.

EXAMPLE 10

Selectivity of Microbioelectrode

The selectivity to a target substance in an amperometric measurement is dependent on the electronic reaction in the microbioelectrode. When the conventional noble metal electrode is used in an amperometric measurement, nonselective response occurs in the measurement of a sample which contains other saccharide and/or amino acid.

When the microbioelectrode of the present invention is used, the selectivity of the microbioelectrode can be improved by forming oxide of noble metal to be used as a conductive layer for the electrode.

Such surface oxide can be formed by polarizing anodically the matrix of the electrode. Therefore, such polarization treatment of the electrode can be referred to as "anodic polarization or anodic treatment".

A platinum wire of 100 micrometer in diameter was sealed on a block of acryl resin, and the surface of the block including the edge surface of the platinum wire was polished by alumina abrasibes having particles of 30 micrometer to 0.05 micrometer in size. It was dipped in a solution of hexachloroplatinate of 3% containing 500 ppm of lead acetate and 10% of glucose oxidase, electrolysis was carried out for five minutes by applying minus 0.08 volt so as to form a deposit of platinum black layer on the edge surface.

Then, one of the microelectrodes which had been prepared as above was further treated by the anodic polarization, that is, treated for ten minutes by applying 1.2 V versus Ag/AgCl electrode to the microbioelectrode so as to form surface oxide on the platinum black layer of the microbioelectrode.

Figure 16A:
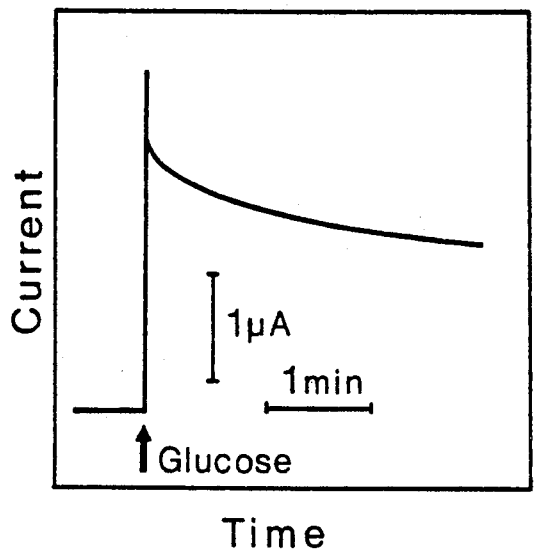
FIG. 16A is a graph showing closely a transient current response as generated by the inventive microbioelectrode which had been cathodically polarized.

FIG. 16A shows the response curve measured by using the microbioelectrode which had not been treated with anodic polarization as mentioned above.

Figure 16B:
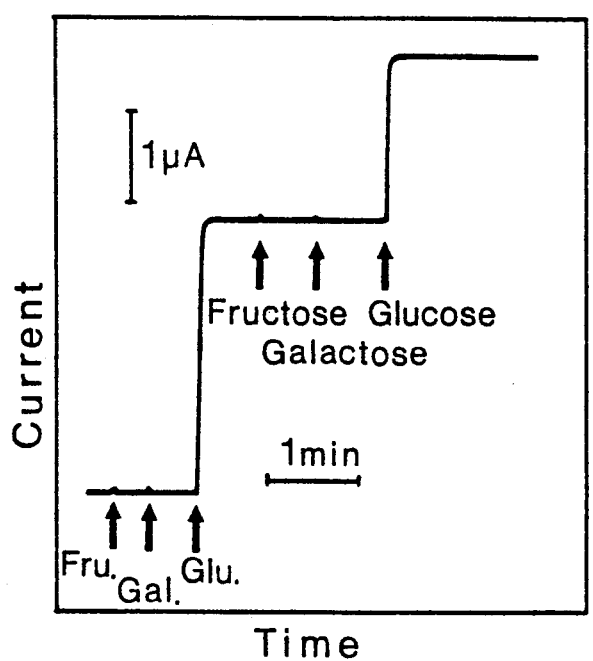
FIG. 16B is a graph showing a response curve measured as measured in the same way for the graph of FIG. 2, by the inventive microbioelectrode which had been anodically polarized, wherein fructose, galactose and glucose were respectively added twice as shown in the graph, in this order, where the measurement was carried out in a batch system.

Further, FIG. 16B shows the response curve measured by using the microbioelectrode having glucose oxidase in its porous layer, which had been treated with anodic polarization at 1.2 V for ten minutes as mentioned above. The response curve was obtained upon the sequential addition of fructose and galactose and glucose in this order.

FIG. 16B evidences that the microbioelectrode which had been treated with the anodic polarization responds significantly only to glucose and does not respond to fructose and galactose.

EXAMPLE 11

Improvement of Selectivity of Microelectrode for Flow Injection Analysis

Improvement of selectivity was also ascertained in a flow injection analysis using the assembly of FIG. 4.

Figure 17B:
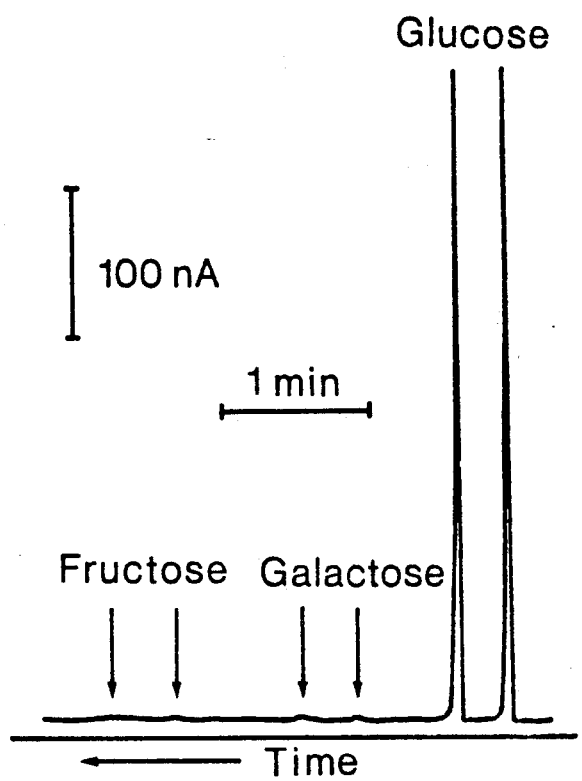
FIGS. 17A and 17B are graphs respectively showing the nonselective responses to saccharides, measured by using the inventive microbioelectrode in a flow system, when the electrode had not been treated after the deposition with the enzyme (FIG. 17B); and the improved selectivity of the response of the inventive microbioelectrode when it had been treated by an anodic polarization so as to improve the feature of the surface oxide of the inventive transducing platinized platinum electrode (FIG. 17A).
Figure 17A:
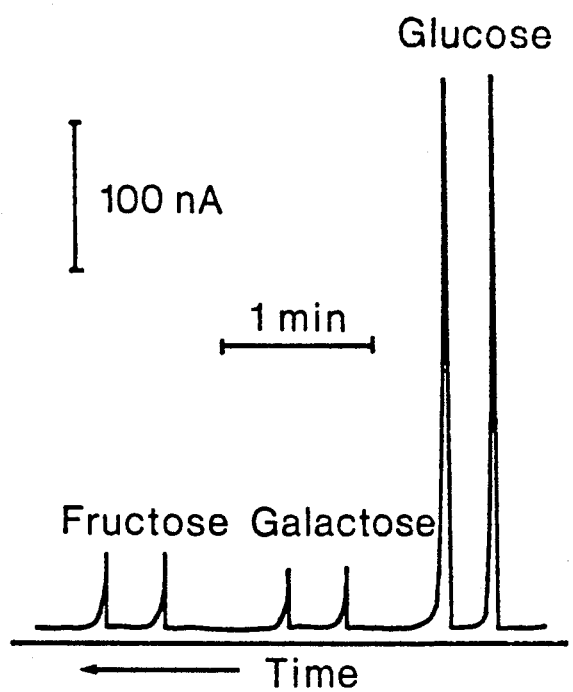

FIG. 17A shows the response curve measured, upon sequential addition of fructose, galactose and glucose in this order, by using the microbioelectrode which incorporated glucose oxidase within the platinum black layer, which electrode had not been treated with anodic polarization and had been assembled in a transducing cell of FIG. 4.

Next, the microbioelectrode was treated with anodic polarization, and then, the response curve was measured by such treated microbioelectrode, and the resulting response curve is shown in a graph of FIG. 17B.

FIGS. 17A and 17B reveal that the anodic polarization treatment in accordance with the present invention improves the selectivity of the microbioelectrode to the target substance (glucose) in measuring even in the presence of other saccharides than glucose. Therefore, it can be concluded that the inventive microbioelectrode is useful in the flow injection analysis.

As described in the foregoings, the inventive method of immobilizing a biologically active substance, the microbioelectrode prepared thereby, and an analytical method using the microbioelectrode can be used for a variety of measuring system, in which system the microbioelectrode functions as a biosensing device, and are adopted not only for the measurement of physiologically active substance, but for analytical instrument, because the microbioelectrode shows extremely rapid response and high sensitivity.

We claim:

1. A biologically active substance immobilized microbioelectrode comprising a fine particle electrically conductive surface layer incorporating an immobilized biologically active substance formed by a single step of:
    depositing fine particles of a conductive material and said active substance on the surface of an electroconductive material so as to form a porous conductive material incorporating said active substance therewithin.

2. The microbioelectrode in accordance with claim 1, further comprising the step of:
    stabilizing the resulting active substance incorporated porous conductive material with a crosslinking agent.

3. The microbioelectrode in accordance with claim 2, further comprising the step of:
    forming a polymeric film on the surface of said conductive materials for the stabilization of said active substance.

4. The microbioelectrode in accordance with claim 1, wherein said porous conductive material is treated by anodic oxidation after the deposition of said porous conductive material incorporating said active substance.

5. The microbioelectrode in accordance with claim 1, wherein said fine particles are deposited by a solution containing the conductive material.

6. The microbioelectrode in accordance with claim 1, wherein said fine particles are deposited by a chemical reaction utilized to generate the conductive material.

7. A microbioelectrode designed to have biologically active substances embodied directly in a transducing electrode, or immobilized in the fine pores or on the surface of a porous electroconductive material which is deposited on the surface of a transducing electrode, whereby both the biochemical reaction and electrochemical reaction occur simultaneously so as to enable direct transduction into an electric signal.

8. A microbioelectrode comprising a fine platinum black electrically conductive surface layer with an immobilized biologically active substance incorporated therein, wherein said microbioelectrode is formed by the single step of depositing particles of said fine platinum black and an active substance on the surface of an electroconductive material.

9. The microbioelectrode in accordance with claim 8, further comprising the step of:
    stabilizing the resulting active substance incorporated porous conductive material with a crosslinking agent.

10. The microbioelectrode in accordance with claim 9, further comprising the step of:
    forming a polymeric film on the surface of said conductive materials for the stabilization of said active substance.

11. The microbioelectrode in accordance with claim 8, wherein said porous conductive material is treated by anodic oxidation after the deposition of said porous conductive material incorporating said active substance.

12. The microbioelectrode in accordance with claim 8, wherein said fine particles are deposited by a solution containing the conductive material.

13. The microbioelectrode in accordance with claim 8, wherein said fine particles are deposited by a chemical reaction utilized to generate the conductive material.

* * * * *